(12) United States Patent
Hughes

(10) Patent No.: US 9,174,026 B1
(45) Date of Patent: Nov. 3, 2015

(54) NEONATAL SYRINGE RETENTION DEVICE

(71) Applicant: Robin Hughes, Renton, WA (US)

(72) Inventor: Robin Hughes, Renton, WA (US)

( * ) Notice: Subject to any disclaimer, the term of this patent is extended or adjusted under 35 U.S.C. 154(b) by 390 days.

(21) Appl. No.: 13/708,187

(22) Filed: Dec. 7, 2012

(51) Int. Cl.
*A61M 5/32* (2006.01)
*A61M 25/02* (2006.01)

(52) U.S. Cl.
CPC ...................................... *A61M 25/02* (2013.01)

(58) Field of Classification Search
CPC .......... A61M 25/02; A61M 2025/026; A61M 2025/0206; A61M 2025/0253; A61M 2025/0266; A61M 2025/0246; A61M 2025/0273
USPC .......................................................... 604/179
See application file for complete search history.

(56) References Cited

U.S. PATENT DOCUMENTS

| | | | |
|---|---|---|---|
| 2,590,006 A * | 3/1952 | Gordon | 604/180 |
| 4,542,965 A * | 9/1985 | Shedrow | 351/57 |
| 4,560,378 A | 12/1985 | Welland | |
| 5,253,393 A | 10/1993 | Levin | |
| 5,344,107 A | 9/1994 | Lee | |
| 5,806,816 A | 9/1998 | Hull et al. | |
| D511,736 S | 11/2005 | Davie | |
| 2006/0089077 A1 | 4/2006 | Wittschen | |
| 2007/0088385 A1 | 4/2007 | Perry | |
| 2010/0180900 A1* | 7/2010 | Talsma et al. | 128/207.14 |

* cited by examiner

*Primary Examiner* — Kevin C Sirmons
*Assistant Examiner* — Deanna K Hall
(74) *Attorney, Agent, or Firm* — Robert C Montgomery; Montgomery Patent & Design

(57) ABSTRACT

A neonatal syringe retention device provides a means to retain a syringe in an elevated location inside of an incubator. The device comprises a suction cup removably attached to an interior wall surface of an incubator. The device also comprises a strap having a distal end comprising an aperture to hold the syringe body, and a proximal end having a plurality of apertures which adjust the overall length of the strap held from the suction cup.

10 Claims, 3 Drawing Sheets

NEONATAL SYRINGE RETENTION DEVICE

RELATED APPLICATIONS

There are no current co-pending applications.

FIELD OF THE INVENTION

The presently disclosed subject matter is directed to retention device for a syringe and more particularly, to a retention device for securing a syringe commonly associated with neonatal care to a support structure such as an incubator.

BACKGROUND OF THE INVENTION

The invention described herein pertains to a securing strap, and more specifically to a neonatal syringe retention device. Often new born children experience unfortunate complications and require air vent or open-ended feeding syringe treatments while inside an incubator. Due to the configuration of an open syringe, the contents can easily spill out when tipped or left on their side. Additionally, any syringe relying on gravity for operation must be suspended in an elevated position. A stable, re-useable device for securing a syringe to a wall of an incubator is needed.

U.S. Pat. App. Pub. No. 2006/0089077 to Joyce F. Wittschen discloses a syringe cover shaped like a teddy bear. The cover secures a syringe and also hides the syringe from a child's view. A syringe is held in an upright position while the cover is in an upright position. However, the cover is not secured to anything else which makes it easy to knock over and also provides no way to secure a syringe in an elevated position.

Another attempt at providing a securing device is disclosed in U.S. Pat. No. 5,253,393 to Norman D. Levin. This patent provides a strap for holding a heavy bag having a suction cup, two (2) "S" hooks and an elongated strap. The elongated strap has a first end and a second end, both ends having apertures for receiving an "S" hook. The first end is connected to the suction cup via an "S" hook, while the second end is connected to the heavy bag via an "S" hook. While this device attaches to a surface using a suction cup and has an elongated strap for securing an item, the "S" hooks are easy to separate from the straps and may cause unintended disconnection of the device. Additionally, the "S" hooks alone cannot be used to secure a syringe in an upright position.

Yet another attempt at providing a securing device is disclosed in U.S. Pat. No. 5,806,816 to Harold L. Hull et al. This patent provides a plurality of suction cups with flexible straps attached thereto. The straps are intertwined and the suction cups pulled tightly in opposing directions. The suction cups are secured to a surface, retaining an object against a surface and under the flexible straps. The securing device disclosed in this patent does not provide a reliable method for securing a syringe and involves the use of multiple suction cups.

Although the various devices observed may fulfill their individual, particular objectives, each device suffers from one (1) or more disadvantage or deficiency related to design or function. Whether taken singly, or in combination, none of the observed devices disclose the specific arrangement and construction of the instant invention.

SUMMARY OF THE INVENTION

The inventor has recognized the deficiencies in the art pertaining to syringe retaining devices. Furthermore, the inventor has observed that there is a need for a device which secures a syringe in an upright position within an enclosed space while also minimizing the risk of the syringe being tipped over.

The inventor has addressed at least one (1) of the problems observed in the art by developing a novel neonatal syringe retention device. It is a feature and aspect of the present invention to provide a flexible strap adjustably secured to a suction cup. The strap has a first end with a plurality of circular openings disposed thereon. Each opening is deformable and able to accommodate the passage there through of a sphere having a greater diameter than the opening. A sphere affixed to the suction cup is passed through a desired circular opening on the strap, detachably securing the strap thereto.

It is a further aspect of the invention to provide a second end on the strap, opposite the first end. The second end has a single deformable opening disposed thereon for securely receiving the body of a syringe. A desired height is chosen through placement of the suction cup and attachment of the first end thereto. Once a desired height is chosen a syringe is passed partially through the opening in the second end of the strap, securing the syringe in that position until removed.

Furthermore, the described features and advantages of the disclosure may be combined in various manners and embodiments as one skilled in the relevant art will recognize. The disclosure can be practiced without one (1) or more of the features and advantages described in a particular embodiment.

Further advantages of the present disclosure will become apparent from a consideration of the drawing and ensuing description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
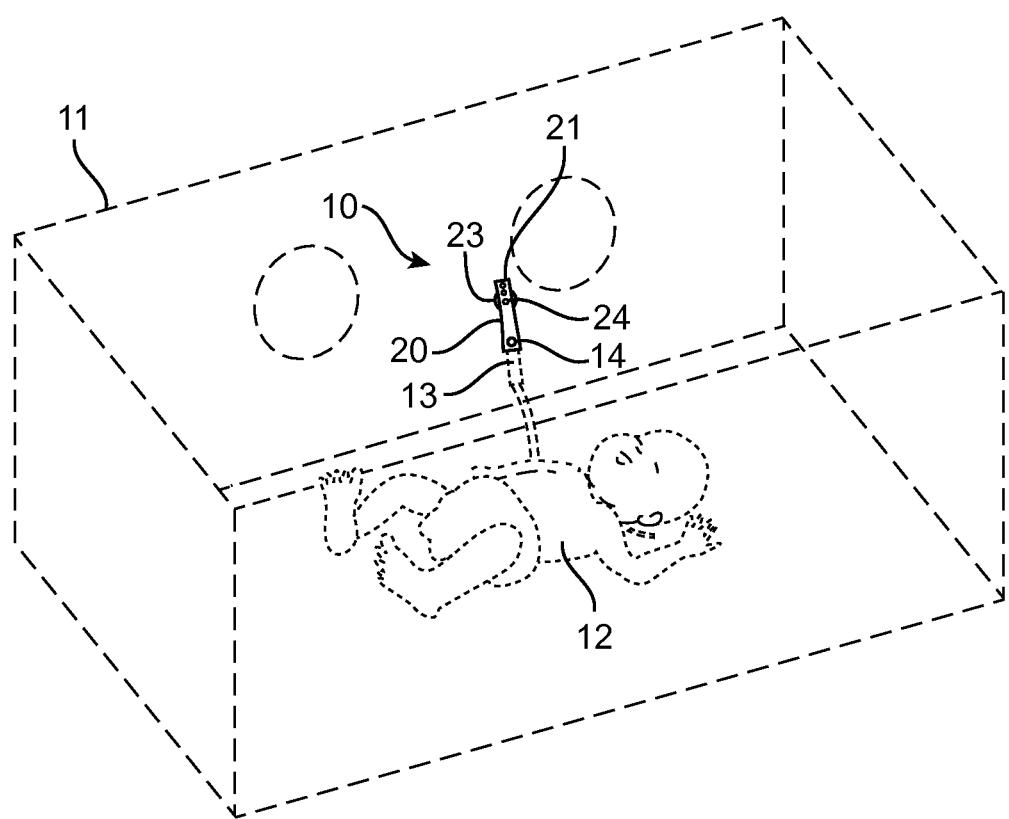
FIG. 1 is an environmental view of a neonatal syringe retention device 10, according to a preferred embodiment of the present invention.

DESCRIPTIVE KEY 10 neonatal syringe retention device
11 incubator
12 infant
13 syringe
14 plunger
20 strap
21 upper aperture
22 lower aperture
23 suction cup
24 protrusion

DETAILED DESCRIPTION OF THE PREFERRED EMBODIMENT

Figure 2:
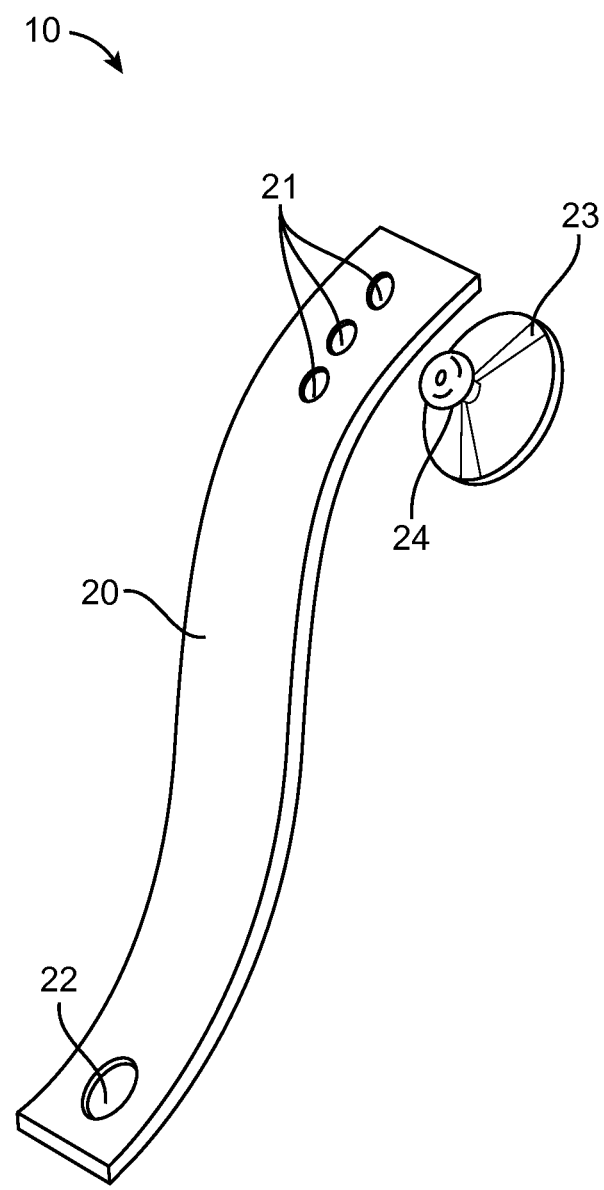
FIG. 2 is a perspective view of the neonatal syringe retention device 10, according to a preferred embodiment of the present invention; and, FIG. 3 is another perspective view of the neonatal syringe retention device 10, according to a preferred embodiment of the present invention.
Figure 3:
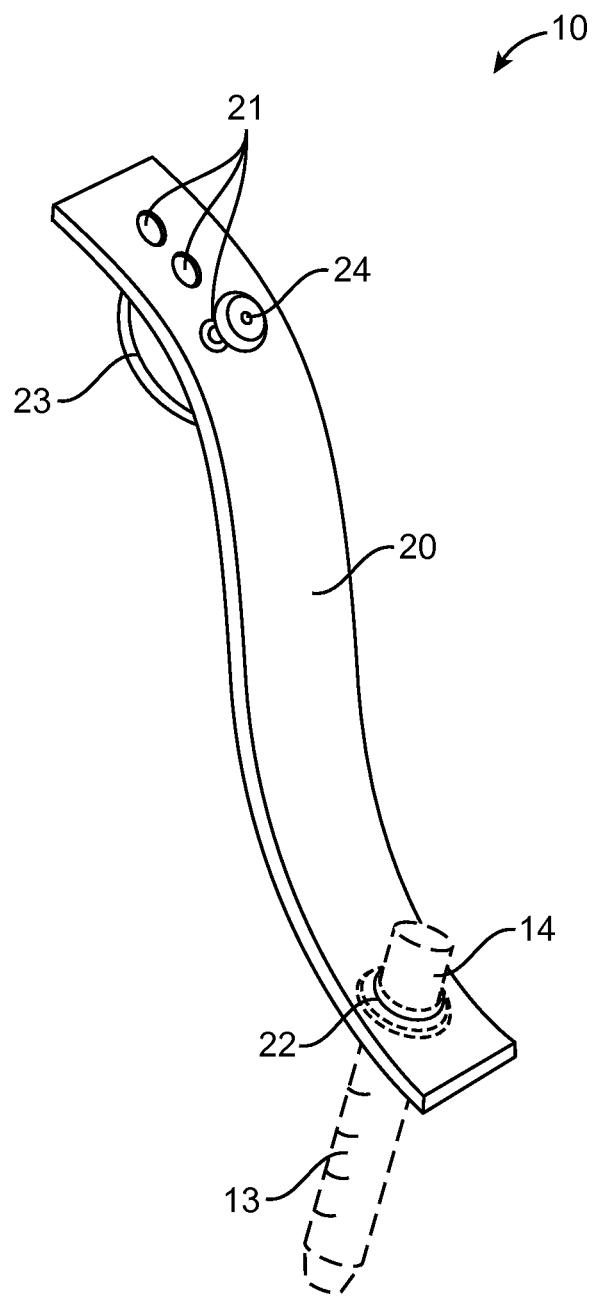

The best mode for carrying out the invention is presented in terms of its preferred embodiment, herein depicted within FIGS. 1 through 3. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes a neonatal syringe retention device (herein described as the "device") 10, which provides a means for securing and suspending a syringe 13 upon an inner wall of an incubator 11 to provide medical treatments to an infant 12.

Referring now to FIG. 1, an environmental view of the device 10, according to the preferred embodiment of the present invention, is disclosed. The device 10 comprises a strap 20 and a suction cup 23. The device 10 enables the existing syringe 13 to be suspended in a secured manner against the inner wall of the incubator 11. The device 10 may be utilized upon various incubators 11 such as a "hands-inside" incubator 11. The device 10 enables various treatments to be administered to infants 12 such as, but not limited to: an "air vent" which is needed for some medical treatments, a "gravity" nasogastric feedings, or the like. The syringe 13 preferably utilized is an open venting type, yet other types may be utilized without liming the scope of the invention. The device 10 prevents stomach content or feeding residuals from spilling out of the syringe 13 because the device 10 maintains the secure upright position of said syringe 13.

Referring now to FIG. 2, a perspective view of the device 10 and FIG. 3, another perspective view of the device 10, according to the preferred embodiment of the present invention, are disclosed. The strap 20 is fabricated from materials which comprise elastic characteristics such as, but not limited to: nitrile, rubber latex, vinyl, or the like. The strap 20 is preferably manufactured in various colors to correspond to various medical coding.

A proximal portion of the strap 20 comprises a plurality of intermediately positioned linear upper apertures 21 which provide an adjustable attachment to the suction cup 23. The suction cup 23 is a common device utilized to temporarily affix an object to a non-porous surface. The suction cup 23, as typically manufactured, comprises a curved or bell-shaped body which creates a partial vacuum seal upon a surface or in this instance upon the inner wall of the incubator 11. An intermediate exterior of the suction cup 23 comprises an upwardly extending protrusion 24. The protrusion 24 is inserted within a desired upper aperture 21 to attach the suction cup 23 to the strap 20. The protrusion 24 is positioned in a manner which orients the suction cup 23 adjacent to the incubator 11.

A distal portion of the strap 20 comprises a lower aperture 22 which provides an attachment to an upper portion of a syringe 13. The syringe 13 is positioned within the lower aperture 22 with a plunger 14 exposed similarly to the above-mentioned protrusion 24.

Due to the elastic characteristic of the strap 20 the apertures 21, 22, it is able to stretch to conform around the protrusion 24 and syringe 13, respectively. Once the protrusion 24 or syringe 13 is removed the apertures 21, 22 return to an un-stretched state.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the device 10, it would be installed as indicated in FIG. 1.

The method of utilizing the device 10 may be achieved by performing the following steps: acquiring the device 10; inserting the protrusion 24 within a desired upper aperture 24; attaching the suction cup 23 to a desired inner wall of an incubator 11; inserting the syringe 13 through the lower aperture 22; administering medical treatments to an infant 12; and, utilizing the device 10 to suspend a syringe 13 inside of an incubator 11 in a manner which is quick, easy, and effective.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A syringe retention device, comprising:
   an elongated elastic strap comprising a flexible material and having a proximal end and a distal end;
   an evenly-spaced plurality of expandable fastener apertures disposed through said elastic strap adjacent to said proximal end and aligned in a longitudinal centerline of said elastic strap;
   a syringe holder adjacent to said distal end of said elastic strap; and,
   a securing fastener removably attached to a selected one of said plurality of fastener apertures;
   wherein said selected one of said plurality of fastener apertures expands to receive said securing fastener and retracts to retain said securing fastener;
   wherein said securing fastener securely fastens said elastic strap to a support surface; and,
   wherein said syringe holder is configured to retain a syringe.

2. The device of claim 1, wherein said securing fastener comprises a suction cup, said suction cup comprising a suction cup body having a suction end and an opposing attachment end.

3. The device of claim 2, wherein said attachment end of said suction cup comprises a protrusion extending outwardly from an intermediate exterior of said suction cup body; and,
   wherein said protrusion is receivably attached within said selected one of said plurality of fastener apertures of said elastic strap.

4. The device of claim 1, wherein said syringe holder comprises a syringe aperture disposed through said elastic strap.

5. The device of claim 4, wherein said elastic strap comprises a nitrile material.

6. The device of claim 4, wherein said strap comprises a rubber latex.

7. The device of claim 4, wherein said strap comprises a vinyl material.

8. The device of claim 1, wherein said elastic strap comprises a nitrile material.

9. The device of claim 1, wherein said strap comprises a rubber latex.

10. The device of claim 1, wherein said strap comprises a vinyl material.

* * * * *